United States Patent [19]

Shoham et al.

[11] Patent Number: 4,704,360

[45] Date of Patent: Nov. 3, 1987

[54] ENZYMATIC DEGRADATION OF LIPOPOLYSACCHARIDE BIOEMULSIFIERS

[75] Inventors: Yuval Shoham, Kibbutz Einat; Eugene Rosenberg, Raanana; David L. Gutnick, Sharon Tichon, all of Israel

[73] Assignee: Petroleum Fermentations, Curacao, Netherlands Antilles

[21] Appl. No.: 557,010

[22] Filed: Nov. 30, 1983

[51] Int. Cl.$^4$ .................. C12N 9/24; C12P 19/14; C12P 19/04; C12R 1/07

[52] U.S. Cl. ..................... 435/99; 435/101; 435/200; 435/253; 435/832; 435/835

[58] Field of Search ............. 435/99, 101, 200, 253, 435/266, 271, 822, 823, 850, 874, 832, 835

[56] References Cited

U.S. PATENT DOCUMENTS

| | | |
|---|---|---|
| 3,941,692 | 3/1976 | Gutnick et al. . |
| 4,230,801 | 10/1980 | Gutnick et al. . |
| 4,234,689 | 11/1980 | Gutnick et al. . |
| 4,311,829 | 1/1982 | Gutnick et al. . |
| 4,311,830 | 1/1982 | Gutnick et al. . |
| 4,311,831 | 1/1982 | Gutnick et al. . |
| 4,380,504 | 4/1983 | Gutnick et al. . |
| 4,395,353 | 7/1983 | Gutnick et al. . |
| 4,395,354 | 7/1983 | Gutnick et al. . |
| 4,432,887 | 2/1984 | Zajic et al. ................. 435/666 |

OTHER PUBLICATIONS

Buchanan et al., *Bergey's Manual of Determinative Bacteriology* 8th ed., Williams & Wilkins Co., Batt.; pp. 249, 250 (1974).
Palmer, Trevor, *Understanding Enzymes*, John Wiley & Sons, New York; pp. 314, 315 (1981).
Zuckerberg et al., 1979, Appl. Environ. Microbiol. 37: 414-420.
Taylor and Juni, 1961, J. Bacteriol. 81: 688-693.
Sutherland, Enzymes Acting on Bacterial Surface Carbohydrates in "Surface Carbohydrates of the Prokaryotic Cell," 1977, ed. Sutherland, 209-245, Academic Press, London.
Dubos and Avery, 1931, J. Exptl. Med. 54; 57-71.
Mitchell and Nevo, 1965, Nature 203: 1007-1008.
Shoham et al., 1983, Appl. Env. Microbiol. 46: 573-579.
Rosenberg et al., 1983, Infect. Immun. 39: 1024-1028.
Rosenberg, 1981, Appl. Environ. Microbiol. 42: 375-377.
Rosenberg, 1981, Infect. Immun. 33: 29-33.

*Primary Examiner*—Lionel M. Shapiro
*Assistant Examiner*—Elizabeth C. Weimar
*Attorney, Agent, or Firm*—Pennie & Edmonds

[57] ABSTRACT

Methods and compositions are provided for the production and use of enzymes that degrade lipopolysaccharide bioemulsifiers, and, in particular, emulsans. The enzymes may be used to demulsify bioemulsifier-stabilized hydrocarbon-in-water emulsions.

29 Claims, 11 Drawing Figures

(o—o) Control Boiled Supernatant + Emulsan (●—●) Untreated Supernatant Containing Emulsanase + Emulsan (o—o) Bacto-tryptone + 1.5% Yeast Extract
(●—●) Bacto-tryptone + 1.0% Yeast Extract
(■—■) Bacto-tryptone + 0.5% Yeast Extract
(□—□) Bacto-tryptone (No Supplement)

(●—●) Control, Boiled Enzyme
(○—○) Emulsanase

ENZYMATIC DEGRADATION OF LIPOPOLYSACCHARIDE BIOEMULSIFIERS

TABLE OF CONTENTS

1. Introduction
2. Background of the Invention
   2.1. Microbial Surface Active Agents
   2.2. Biopolymer-Degrading Microorganisms
   2.3. Adherence of Bacteria to Hydrophobic Surfaces
3. Summary of the Invention
4. Nomenclature
5. Brief Description of the Figures
6. Detailed Description of the Invention
   6.1. Isolation of Microorganisms that Produce Lipopolysaccharide Bioemulsifier-Degrading Enzymes
      6.1.1. Isolation of Emulsanase-Producing Microorganisms
   6.2. Use of Lipopolysaccharide Bioemulsifer-Degrading Enzymes
      6.2.1. Use of Emulsanase
   6.3. Preparation and Use of Emulsan Enzymatic Degradation Products
7. Examples
   7.1. Isolation and Growth of an Emulsanase-Producing Bacterium
      7.1.1. Growth of a Mixed Culture from Soil
      7.1.2. Degradation of Emulsan by the Mixed Cultures
      7.1.3. Degradation of Emulsan by a Mixed Culture Cell-Free Supernatant Fluid
      7.1.4. Isolation of a Pure Culture of an Emulsan-Degrading Bacterium from Mixed Bacterial Culture
      7.1.5. Properties of the YUV-1 Bacterium
   7.2. Partial Purification and Characterization of Emulsanase
      7.2.1. Isolation of Emulsanase from YUV-1
      7.2.2. Characterization of Fraction F-10 Emulsanase
   7.3. Correlation of the Viscosity, Emulsifying Activity and Molecular Size of Emulsion During Its Enzymatic Degradation
   7.4. Breakage of Preformed Emulsions by Emulsanase
   7.5. Characterization of the Products of the Exhaustive Enzymatic Degradation of Emulsan
   7.6. Inhibition of Bacterial Adherence By the Enzymatic Degradation Products of Emulsan
      7.6.1. Interference with Adhesion to Epithelial Cells
      7.6.2 Interference With Adhesion to Hydrocarbons
   7.7. Deposit of Microorganism

INTRODUCTION

This invention relates to microbial enzymes that degrade microbially-produced interfacially-active bioemulsifiers and more particularly to microbial enzymes that degrade emulsans. This invention also relates to the use of these enzymes for the enzymatic degradation of microbial bioemulsifiers used to stabilize hydrocarbon-in-water emulsions, thereby effecting demulsification.

Bioemulsifier-stabilized hydrocarbon-in-water emulsions, so called "hydrocarbosols", are likely to become increasingly important in the future, since they can be produced from heavy petroleum oils that are otherwise too viscous for handling by ordinary transportation or pipeline technology. Because these bioemulsifier-stabilized emulsions are exceptionally stable and resistant to phase separation, they can be subjected both to the severe stress of pumping through long pipelines and to long periods of standing without breaking of the emulsion.

This extreme stability of bioemulsifier-stabilized emulsions, while desirable for transport, handling and/or storage, potentially poses problems for ultimate hydrocarbon recovery. Ordinarily, this recovery must be accomplished by breaking the emulsion by chemical treatment or through the application of thermal energy. This invention permits the facile breaking of microbial bioemulsifier-stabilized emulsions through enzymatic degradation under mild conditions.

This invention also relates to the lipo-oligosaccharidic fragments produced by enzymatic degradation of the family of bioemulsifiers known as emulsans and to the use of these fragments for the prevention or elimination of bacterial adhesion. Although the fragments lose substantially all bioemulsifying activity, i.e., activity as emulsion stabilizers, they retain an ability to interfere with the adhesion of bacteria to hydrocarbon and/or other hydrophobic surfaces. This property should find application in medicine, dentistry and in other areas.

2. BACKGROUND OF THE INVENTION

2.1. MICROBIAL SURFACE ACTIVE AGENTS

Numerous microorganisms can multiply by using hydrocarbons as a primary carbon source. Because of the immiscibility of hydrocarbons with the aqueous environment, these microorganisms produce surface active and/or emulsifying agents that convert the insoluble, oily substrates into fine oil-in-water emulsions. The result is a marked increase in the effective hydrocarbon surface area, through which far more effective assimilation and metabolism may occur.

Among the microbes with this ability is *Mycobacterium rhodochrous* NCIB 9905, which Holdom et al. [J. Appl. Bacteriol. 32, 448 (1969)] showed produces a nonionic surface active agent during growth on n-decane. Iguchi et al. [Agric. Biol. Chem. 33, 1657 (1969)] found that *Candida petrophilium* produced a surface active agent consisting of peptides and fatty acid residues, while Suzuki et al. [Agric. Biol. Chem. 33, 1619 (1969)] reported that trehalose lipid appeared in the oil phase of cultures of various Arthrobacter, Brevibacterium, Corynebacterium and Norcardia strains. Wagner has reported the production of trehalose lipids by *Norcardia rhodochrous* and *Mycobacterium phlei* and their use in oil recovery [U.S. Pat. Nos. 4,392,892 and 4,286,660].

*Torulopsis gropengiesseri* was found to produce a sophorose lipid, while rhamnolipids are reported by K. Hisatsuka et al. [Agric. Biol. Chem., 35, 686 (1971)] to have been produced by *Pseudomonas aeruginosa* strain S7B1 and by S. Itoh et al. [Agric. Biol. Chem., 36, 2233 (1971)] to have been produced by another *P. aeruginosa* strain, KY4025. The growth of *Corynebacterium hydrocarboclastus* on kerosene was reported by J. E. Zajic and his associates [Dev. Ind. Microbiol., 12, 87 (1971); Biotechnol. Bioeng., 14, 331 (1972); Chemosphere 1, 51 (1972); Crit. Rev. Microbiol, 5, 39; U. S. Pat. No. 3,997,398] to produce an extracellular heteropolysaccharide which, among other properties, emulsified kerosene, Bunker C fuel oil and other fuel oils.

Gutnick et al. showed that Acinetobacter sp. ATCC 31012 (RAG-1) produces polyanionic protein-associated lipopolysaccharide biopolymers with strong activity as emulsion stabilizers. These interfacially active agents, collectively called emulsans, encapsulate the bacteria and are also released to the surrounding medium. The growth of Acinetobacter sp. ATCC 31012 on ethanol or on fatty acid salts produces α-emulsans [U.S. Pat. Nos. 4,230,801; 4,234,689 and 4,395,354], while the use of crude oil or hexadecane as a carbon source leads to the production of β-emulsans [U.S. Pat. No. 3,941,692]. The α-emulsans and β-emulsans can be derivatized to an O-deacylated form called Ψ-emulsans [U.S. Pat. No. 4,380,504]. The α-emulsans, β-emulsans and Ψ-emulsans can be deproteinized to yield apo-α-emulsans, apo-β-emulsans and apo-Ψ-emulsans, respectively [U.S. Pat. Nos. 4,311,830; 4,311,829 and 4,311,831, respectively].

The emulsion-stabilizing properties of emulsans have recently been applied to the utilization of highly viscous hydrocarbons by Hayes et al. [U.S. patent application Temporary Ser. No. 547,892] who demonstrated that emulsans can be used in conjunction with chemical surfactants to convert heavy crude oils to low visocity oil-in-water emulsions. Such emulsan-stabilized emulsions are exceptionally stable and thus suitable for transport by truck, tanker, or conventional pipeline technology.

2.2 BIOPOLYMER-DEGRADING MICROORGANISMS

It has long been known that many bacteria can degrade complex microbial biopolymers and thus utilize them as carbon sources. For example, Dubos and Avery [J. Exptl. Med. 54, 57 (1931)] first showed that a soil bacillus could be grown on the polysaccharide from Streptococcus pneumoniae type III. Later, Shaw and Sickles [J. Immunol. 64, 27 (1950)] prepared an isolate of another soil bacillus that could grow on either type III or type VIII pneumococcal polysaccharide. Mitchell and Nevo [Nature 203, 1007 (1965)] used Mediterranean sea water as a source of microorganisms that could degrade various capsular polysaccharides. One isolate utilized the capsular polysaccharide of Flavobacterium as its sole carbon source, while still others could metabolize the capsules of Azotobacter, Rhizobium and Arthrobacter, and the cell walls of E. coli B.

Other microorganisms can utilize complex microbial lipopolysaccharides as carbon sources. For example, Nigam et al. [Hoppe-Seylers Zeitschrift füt Physiologische Chemie 351, 1123 (1970)] reported that protozoa and the amoebal forms of the slime mold Dictyostelium discoideum can degrade the cell walls of Salmonella, utilizing the lipid components but excreting the polysaccharide intact. Zajic et al. [Biotechnol. Bioeng. 19, 1303 (1977)] have isolated a Flavobacterium breve and a Flavobacterium devorans that can partially reduce the bioemulsifying activity of a protein-associated lipopolysaccharide complex from Corynebacterium hydrocarboclastus. No attempt was made to isolate or to characterize the responsible enzymes.

Lipopolysaccharide-degrading activities have also been associated with bacteriophages that often must penetrate through thick host capsules. For example, Reske et al. [European J. Biochem. 36, 167 (1973)] have described the phage-induced enzymatic hydrolysis of the lipopolysaccharide of E. coli, in which the polysaccharide skeleton was degraded into fragments. Similarly, Robbins et al. [J. Biol. Chem. 240, 384 (1965)] have reported the phage-induced degradation of the lipopolysaccharide of Salmonella anatum.

Sutherland [Enzymes Acting on Bacterial Surface Carbohydrates, in Surface Carbohydrates of the Prokaryotic Cell (I. Sutherland, ed.), 209–245. Academic Press, London (1977)] has reviewed the general subject of the microbial degradation of complex biopolymers.

2.3. ADHERENCE OF BACTERIA TO HYDROPHOBIC SURFACES

The ability of bacteria to adhere to hydrophobic surfaces appears to be related to a number of important processes. For example, Ofek and Beachey [General Concepts and Principles of Bacterial Adherence in Animals and Man, in Bacterial Adherence (E.H. Beachey, ed.), 1–31. Chapman and Hall, London (1980)] have reported that the adherence of microorganisms to host tissues is a prerequisite for subsequent colonization, and thus is a critical factor in the disease process. Faris et al. [Curr. Microbiol. 5, 67 (1981)] have shown that hydrophobic interactions are involved in the binding of E. coli to mammalian cells, and similar findings have been made for Salmonella typhimurium [Perers et al., Acta Pathol. Microbiol. Scand. Sect. B 85, 308 (1977)] and for streptococci [Alkan et al., Infect. Immun. 18, 555 (1977)].

It has also been suggested by Van Oss [Ann. Rev. Microbiol. 32, 19] that cell surface hydrophobicity may be an important factor in phagocytosis. Furthermore, Weiss et al. [Curr. Microbiol. 7, 125 (1982)] have suggested a role for hydrophobic interactions in the adherence of oral bacteria to tooth enamel, since 72 percent of the bacterial strains recovered from human tooth surfaces were hydrophobic.

The hydrophobicity of bacterial strains may be readily demonstrated experimentally. For example, Rosenberg [Appl. Environ. Microbiol. 42, 375 (1981)] developed a simple assay method based upon the adherence of bacteria to polystyrene surfaces. Moreover, Rosenberg et al. [Infect. Immun. 33, 29 (1981)] have developed experimental systems for the study of the hydrophobic adherence of Acinetobacter calcoaceticus RAG-1 (ATCC 31012) and Streptococcus pyogenes to human buccal epithelial cells and to hydrocarbon droplets. Rosenberg and Rosenberg [J. Bacteriol. 148, 51 (1981)] also showed that an A. calcoaceticus RAG-1 (ATCC 31012) mutant that could not adhere to hexadecane was also unable to bind to epithelial cells.

Because of the importance of microbial hydrophobic adherence to replicative and disease processes, its elimination could be desirable in certain applications. Recently, Rosenberg et al. [Infect. Immun. 39, 1024 (1983)] have shown that emulsan can markedly inhibit the adherence of Acinetobacter calcoaceticus RAG-1 (ATCC 31012) and BD 413, and Streptococcus pyogenes M-5, either to human buccal epithelial cells or to octane. The degree of interference with adherence was the same, whether the emulsan was used to prevent binding or added later, to desorb already bound bacteria.

3. SUMMARY OF THE INVENTION

This invention provides microbial enzymes for the specific degradation of microbially-produced interfacially-active lipopolysaccharide bioemulsifiers. Methods are provided for the isolation by selective growth techniques of lipopolysaccharide bioemulsifier-degrading microorganisms. Methods are also provided for the microbial production and partial purification of enzymes that degrade lipopolysaccharide bioemulsifiers. In a preferred embodiment, bacterial strain YUV-1 (NRRL B-15617) is grown in emulsan-containing medium to produce emulsanase, an enzyme that degrades emulsans by cleaving the glycosidic linkages of the poly-[D-galactosamine/aminouronic acid]-saccharide backbone of the bioemulsifier.

This invention further provides for the use of such enzymes to degrade interfacially-active lipopolysaccharide bioemulsifers in aqueous solution. Alternative methods are provided for the enzymatic degradation of preformed lipopolysaccharide bioemulsifier-stabilized hydrocarbon-in-water emulsions, wherein the bioemulsifiers surround the hydrocarbon droplets and are tightly bound at the hydrocarbon/water interface. As a result, essentially complete phase separation, i.e., demulsification, may be achieved, with nearly quantitative hydrocarbon recovery.

Products of the exhaustive enzymatic degradation of lipopolysaccharide bioemulsifers, and in particular, the emulsans, are also provided, along with methods for their use to interfere with the adherence or adsorption of microorganisms to epithelial cells, hydrocarbons or to other hydrophobic surfaces. This interference may be used prophylactically to prevent adherence or applied after microbial adherence has occurred to desorb microorganisms.

4. NOMENCLATURE

The term "bioemulsifier" is defined as any biologically derived substance which, by virtue of any combination of characteristics including, but not limited to, high molecular weight, polymeric nature, highly specific three-dimensional structure, hydrophobic and hydrophilic moieties and sparing solubility in hydrocarbons, binds tightly to the hydrocarbon/water interface and essentially covers the surface of individual hydrocarbon droplets in hydrocarbon-in-water emulsions, effectively maintaining discrete droplets and preventing coalescence, and thereby imparting substantial stability to hydrocarbon-in-water emulsions. An example of a bioemulsifier is $\alpha$-emulsan.

The term "biosurfactant" is defined as any biologically derived substance which reduces the interfacial tension between water and a hydrocarbon and, as a result, reduces the energy requirement (mixing energy) for creation of additional interfacial area. An example of a biosurfactant is a glycolipid.

The term "lipopolysaccharide bioemulsifier-degrading enzyme" is defined as any enzyme of microbial origin, including but not limited to bacterial or viral origin, that can split the glycosidic bonds of microbial lipopolysaccharide bioemulsifiers to yield non-bioemulsifying breakdown products. Lipopolysaccharide bioemulsifier-degrading enzymes can be used to effect enzymatic destabilization, demulsification or breakage of lipopolysaccharide bioemulsifier-stabilized hydrocarbon-in-water emulsions.

The term "emulsanase" is defined as any enzyme of microbial origin, including but not limited to bacterial or viral origin, that can split the glycosidic bonds of the poly-[D-galactosamine/aminouronic acid]-saccharide backbone of the bioemulsifiers collectively known as emulsans, to produce lipo-oligosaccharidic fragments that are generally from about 1,000 to about 62,000 daltons in size. Such fragments retain little of the bioemulsifying activity, i.e., activity as emulsion stabilizers, exhibited by the native emulsan biopolymers and show markedly decreased viscosity.

The term "hydrocarbosol" is defined as any bioemulsifier-stabilized hydrocarbon-in-water emulsion wherein the individual hydrocarbon droplets are essentially surrounded or covered by water-soluble bioemulsifier molecules predominantly residing at the hydrocarbon/water interface, which bioemulsifier molecules form an effective barrier against droplet coalescence and hence promote the maintenance of discrete hydrocarbon droplets suspended or dispersed in the continuous, low-viscosity aqueous phase.

The term "emulsanosol" is defined as a creamy layer that forms atop an emulsan-stabilized hydrocarbon-in-water emulsion when the emulsion is permitted to stand without agitation for a prolonged period of time, due to the buoyant properties of the dispersed, emulsan-coated hydrocarbon droplets. The energy required to reestablish a fully dispersed emulsion from an emulsanosol-containing system is far below that needed for the establishment of an initial emulsion.

The term "emulsans" is defined as a group of extracellular protein-associated lipoheteropolysaccharides with bioemulsifying activity, i.e., activity as emulsion stabilizers, that is produced by Acinetobacter sp. ATCC 31012 (RAG-1) and its mutants. The group of emulsans may be further categorized into subgroups, on the basis of their carbohydrate, lipid and protein compositions.

The term "$\alpha$-emulsans" defines those extracellular microbial protein-associated lipopolysaccharides produced by Acinetobacter sp. ATCC 31012 and its mutants in which the lipopolysaccharide components (i.e., without the associated protein) are substantially completely N-acylated and partially O-acylated heteropolysaccharides made up of major amounts of D-galactosamine and an aminouronic acid, the lipopolysaccharide components containing at least 5 percent by weight of fatty acid esters in which the fatty acids contain acetyl and longer fatty acid esters, from about 10 to about 18 carbon atoms in chain length. The deproteinized $\alpha$-emulsans are called "apo-$\alpha$-emulsans".

The term "$\beta$-emulsans" defines those extracellular microbial protein-associated lipopolysaccharides produced by Acinetobacter sp. ATCC 31012 and its mutants in which the lipopolysaccharide components (i.e., without the associated protein) are completely N-acylated and partially O-acylated heteropolysaccharides made up of major amounts of D-galactosamine and an aminouronic acid, the lipopolysaccharide components containing less than 5 percent by weight of fatty acid esters in which (1) the fatty acids contain from about 10 to about 18 carbon atoms; and (2) less than 50 percent by weight of such fatty acids are composed of 2-hydroxydodecanoic acid. The deproteinized $\beta$-emulsans are called "apo-$\beta$-emulsans".

The term "$\Psi$-emulsans" defines the O-deacylated extracellular protein-associated microbial polysaccharides obtained from the emulsans, the protein-free components of such $\Psi$-emulsans being completely N-acylated heteropolysaccharides made up of major amounts of D-galactosamine and an aminouronic acid and containing from 0 to 1 percent of fatty acid esters in which, when present, the fatty acids contain from about 10 to about 18 carbon atoms. These protein-free components are called "apo-$\Psi$-emulsans", regardless of how they are prepared.

5. BRIEF DESCRIPTION OF THE FIGURES

To more fully comprehend the invention, reference should be made to the accompanying figures, in which FIG. 1 is a photograph of a petri plate showing plaque formation by strain YUV-1 inoculated at various times (12 hour intervals) onto a lawn of *A. calcoaceticus* RAG-1. Plaque size varies with the time of inoculation: the larger the plaque (i.e., the zone of clearing), the earlier the time of inoculation;

Figure 10:
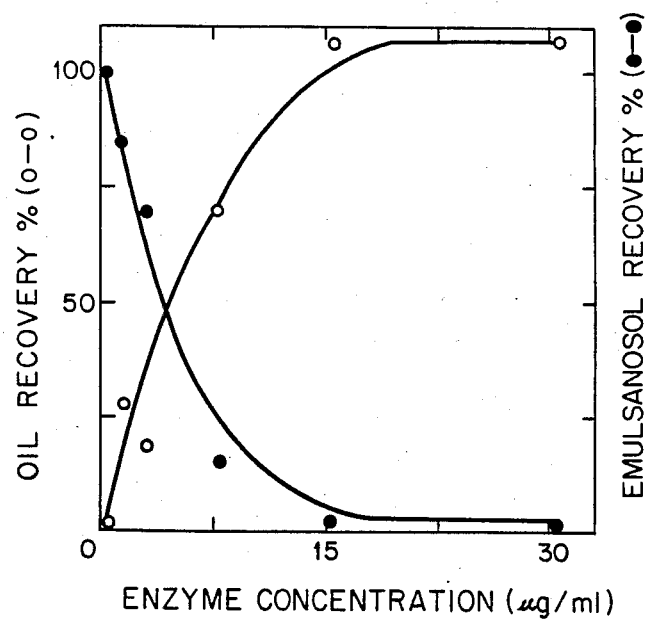
Figure 11:
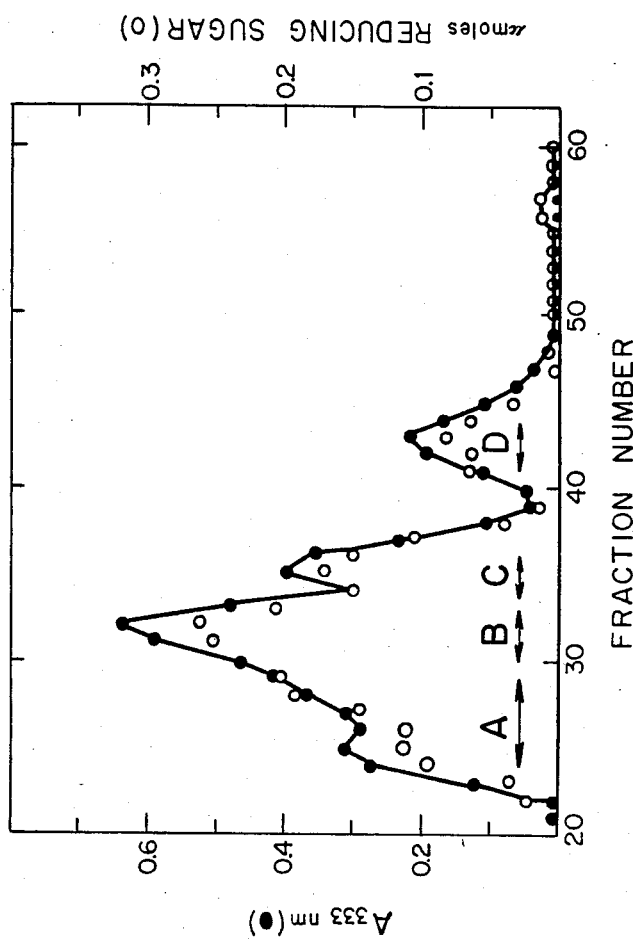

FIG. 10 is a graphical representation of the recovery of hydrocarbon from an established emulsion after emulsanase treatment. The percent recoveries of hydrocarbon and emulsanosol are both shown as functions of emulsanase concentration; and FIG. 11 is a graphical representation of the fractionation of an exhaustive enzymatic digest of emulsan by gel chromatography in Bio-Gel, P-6, showing the elution profile as a function of fraction ultra-violet absorbance and reducing sugar analysis.

6. DETAILED DESCRIPTION OF THE INVENTION

6.1. ISOLATION OF MICROORGANISMS THAT PRODUCE LIPOPOLYSACCHARIDE BIOEMULSIFIER-DEGRADING ENZYMES

A wide variety of naturally occurring microorganisms, including, but not limited to bacteria, viruses, yeast, fungi or protozoans, or genetically engineered microorganisms, with the ability to degrade and/or utilize as carbon and energy sources heteropolysaccharides, homopolysaccharides, lipoheteropolysaccharides and/or lipohomopolysaccharides can potentially serve as a source of lipopolysaccharide bioemulsifier-degrading enzymes. Naturally occurring enzyme-producing lipopolysaccharide-degrading microorganisms can be isolated from sources such as soil, fresh water or salt water by subjecting natural populations of microorganisms to selective pressures in continuous culture, successive batch transfers, or on agar plates.

Selective pressure can be created by exposing a natural mixed microbial population to an otherwise nutritionally complete medium containing as sole carbon and energy source a particular polysaccharide, lipopolysaccharide, oligosaccharide, lipo-oligosaccharide, or even a trisaccharide or disaccharide. A capsule or other polysaccharide of microbial origin, including ones that exhibit bioemulsifier activity, may also serve as sole carbon and energy source to isolate enzyme-producing lipopolysaccharide-degrading strains. Organisms that may produce bioemulsifiers have been discussed by Hayes et al. [U.S. patent application Temporary Ser. No. 547,892, filed Nov. 2, 1983, hereby incorporated by reference]. Those that produce polysaccharide-type compounds include members of the genuses Acinetobacter, Arthrobacter, Pseudomonas, Xanthomonas, Methylomonas, Lactobacillus, and Yersinia.

After repeated exposure to the selective conditions, individual isolates can be purified from the mixed population by techniqes known in the art, cultivated in media similar to that used for isolation, and further tested for their ability to enzymatically degrade lipopolysaccharide bioemulsifiers. By way of illustration, isolates that produce extracellular lipopolysaccharide bioemulsifier-degrading enzymes can be screened by contacting cell-free supernatant culture broths with the lipopolysaccharide bioemulsifier substrate of interest and measuring increased reducing end groups, decreased viscosity and/or decreased bioemulsifier activity.

As an alternative to isolating enzyme-producing strains from nature, microorganisms of the genuses Bacillus or Flavobacterium, or bacteriophage that infect capsule-bearing bacterial strains such as Acinetobacter sp., *E. coli* or Salmonella species, may be screened for production of lipopolysaccharide bioemulsifier-degrading enzymes.

6.1.1. ISOLATION OF EMULSANASE-PRODUCING MICROORGANISMS

Emulsanase-producing microorganisms can be isolated from any natural source provided that the source selected contains at least one microbial strain with the ability to cleave the heteropolysaccharidic structural backbone of members of the emulsan family and their derivatives.

For the purposes of enrichment culture, any of the heteropolysaccharide biopolymers producible by Acinetobacter sp., particularly *Acinetobacter calcoaceticus* and more particularly *Acinetobacter calcoaceticus* RAG-1 (ATCC 31012), may be used as carbon and energy sources and also as substrate in enzymes assays. Acinetobacter heteropolysaccharide biopolymers include, but are not limited to, polyanionic heteropolysaccharide biopolymers, α-emulsans, β-mulsans, Ψ-emulsans, apo-α-emulsans, apo-β-emulsans and apo-Ψ-emulsans defined in Section 4 and described in U.S. Pat. Nos. 4,395,353; 3,395,354; 3,941,692; 4,380,504; 4,311,830; 4,311,829; and 4,311,831; respectively (hereby incorporated by reference) and also heteropolysaccharide biopolymers produced by *Acinetobacter calcoaceticus* BD4 [Taylor and Juni, J. Bacteriol. 81, 688 (1961), hereby incorporated by reference]. Particularly preferred Acinetobacter heteropolysaccharide biopolymers are the α-emulsans, further described in U.S. Pat. Nos. 4,230,801 and 4,234,689 (hereby incorporated by reference).

Figure 1:
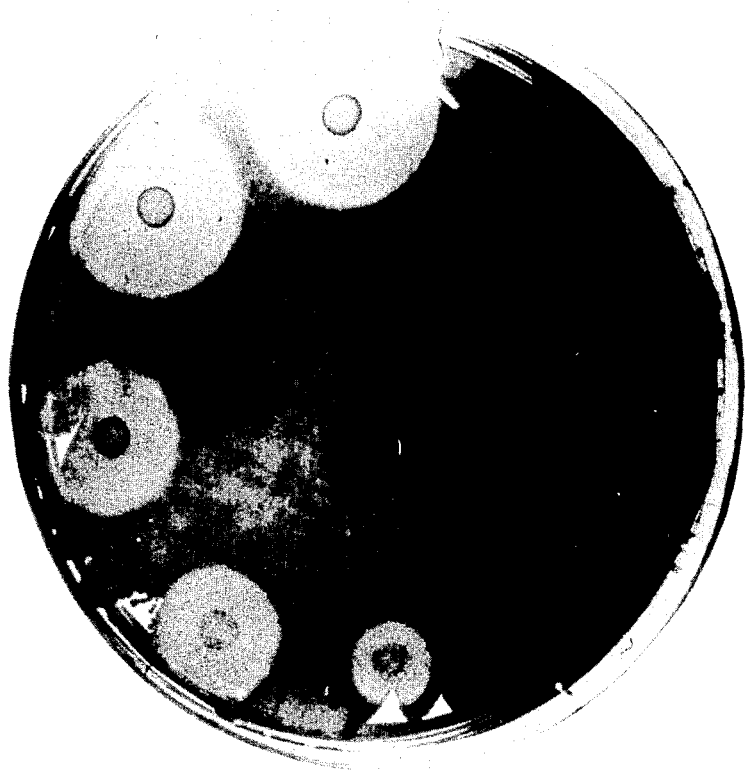

In an illustrated embodiment of this invention, the presence of an emulsanase producing bacterium, both in the initial crude mixture and in isolates obtained by dilution thereof, was shown by the ability to cause a reduction in the viscosity of α-emulsan solutions. Other screening methods that may be quicker and applicable to larger numbers of isolates can also be employed. For example, isolate samples can be spotted on emulsan-producing bacterial lawns, and plaque-forming strains can thereby be selected. The plaque is often due to the secretion of an emulsanase [Shoham and Rosenberg, Appl. Env. Microbiol. 46(3), 573 (1983)]. An example is shown in FIG. 1.

Once an emulsanase-producing strain has been identified, it may be grown, as was the YUV-1 example microorganism in 2% Bacto agar with 1.0% Bacto-tryptone and 0.5% yeast extract. Growth in other agar formulations or in liquid media with a wide range of compositions is also possible. A few possibilities are listed in Table I. It is to be understood that media which support growth do not necessarily provide for enzyme production. For example, for YUV-1, emulsan must be present in the media for emulsanase enzyme to be produced. Presumably emulsan acts as an inducer of the enzyme. Therefore, it is possible that other compounds may be found to act as inducers as well.

TABLE I

POSSIBLE GROWTH MEDIA FOR EMULSANASE PRODUCING MICROORGANISMS

| | |
|---|---|
| 1.0% | Bacto-tryptone |
| 1.0% | Yeast Extract |
| 1.0% | Bacto-tryptone + 0.5% Yeast Extract |
| 1.0% | Bacto-tryptone + 1.5% Yeast Extract |
| 1.0% | Bacto-tryptone + 0.5% Yeast Extract + 0.5% Casitone |
| 1.0% | Yeast Extract + 0.5% Glucose. |

Growth on media containing substitutes for yeast extract might also be possible, using casein, crude serum fractions or other protein sources. It may also be possible to stimulate growth by the addition of utilizable sugars, such as glucose, and certain mineral salts, such as magnesium and phosphate salts.

Although the production of emulsanase may be promoted by growth of the emulsanase-producing microbe on Acinetobacter calcoaceticus RAG-1 (ATCC 31012) lawns as detailed supra, it should be clear that lawns of any emulsan producing bacterial strain could be used instead. Acinetobacter calcoaceticus strains 92 and 312 described by Pines and Gutnick [Arch. Microbiol. 130, 129 (1981)] are but two further examples. If it is desired to extract emulsanase from agar bacterial lawns, a wide range of buffer ionic strengths and salt compositions can be employed.

Moreover, this invention is not restricted to the extraction of emulsanase from agar bacterial lawns. It would be equally feasible instead to grow YUV-1 or a comparable organism in nutritionally complete emulsan-containing liquid medium, given sufficient quantities of suitably pure emulsan which may be prepared by methods described in U.S. Pat. Nos. 4,230,801 and 4,234,689 (incorporated by reference supra). In liquid media containing emulsan, nutritional completeness can be provided by the addition of a complex additive such as yeast extract or, if the nutritional requirements of the microorganism are determined, by the addition of specific nutritional factors such as vitamins and minerals.

In the illustrated methods of emulsanase purification, ammonium sulfate precipitation or ultrafiltration are used. It should of course be appreciated that precipitation with other salts such as sodium sulfate or the use of alternative biochemical separation techniques, including but not limited to ion-exchange chromatography, gel filtration, isoelectric focusing and preparative electrophoresis, could be equally applicable.

6.2. USE OF LIPOPOLYSACCHARIDE BIOEMULSIFIER-DEGRADING ENZYMES

The use of bioemulsifier-stabilized hydrocarbon-in-water emulsions, or hydrocarbosols, to facilitate utilization of highly viscous hydrocarbons was extensively detailed by Hayes et al. in U.S. patent application Temporary Ser. No. 547,892 (incorporated by reference, supra). While low viscosity, bioemulsifier-stabilized hydrocarbon-in-water emulsions are ideal for transportation, storage or other handling procedures, it may be desirable to demulsify or break the emulsion to recover the hydrocarbon fraction. This may also be true for bioemulsifier-stabilized emulsions formulated with less viscous hydrocarbons. Enzymatic demulsification of hydrocarbon-in-water emulsions may be used as an alternative to chemical emulsion breaking or energy-intensive demulsification by heating. Enzymatic demulsification may be achieved by introducing into the aqueous phase of the hydrocarbon-in-water emulsion an affective amount of purified or partially purified bioemulsifier-degrading enzyme, or crude preparations of cell-free culture broths harvested after growth of the producing organism. By breaking glycosidic linkages of the lipopolysaccharide bioemulsifier, e.g. by hydrolysis or elimination mechanisms, the enzyme degrades the bioemulsifier at the hydrocarbon/water interface surrounding the hydrocarbon droplets. Loss of bioemulsifier at the hydrocarbon/water interface results in destabilization and ultimately in coalescence of the hydrocarbon phase which can be recovered for further use.

6.2.1. USE OF EMULSANASE

No commercial enzymes have been found that can degrade emulsan. Thus this particular embodiment of the invention as exemplified by the emulsanase enzyme produced by YUV-1 is uniquely suited to emulsan degradation. Although the true structure of emulsan is not completely known, Zuckerberg et al. [Appl. Environ. Microbiol. 37, 414 (1979)] have indicated that it appears to consist of a heteropolysaccharide backbone with D-galactosamine, aminouronic acid and a third unidentified aminosugar, with fatty acid side chains joined through O-ester and N-acyl linkages.

The use of the emulsanase of this invention encompasses the degradation not only of what is referred to as emulsan, but also the degradation of the specific α, β and Ψ forms of emulsan as defined under the Nomenclature Section, supra. It must also be noted that the emulsans all contain approximately 15 percent by weight protein. As shown by Zuckerberg et al., supra, this protein may be removed by phenol without the loss of emulsifying activity to produce the apo emulsan derivatives. All of these derivatives, together with any others that may be produced wherein the basic aminosugar-aminouronic acid linkages are retained, are usable as substrates in this embodiment of the invention.

Figure 2:
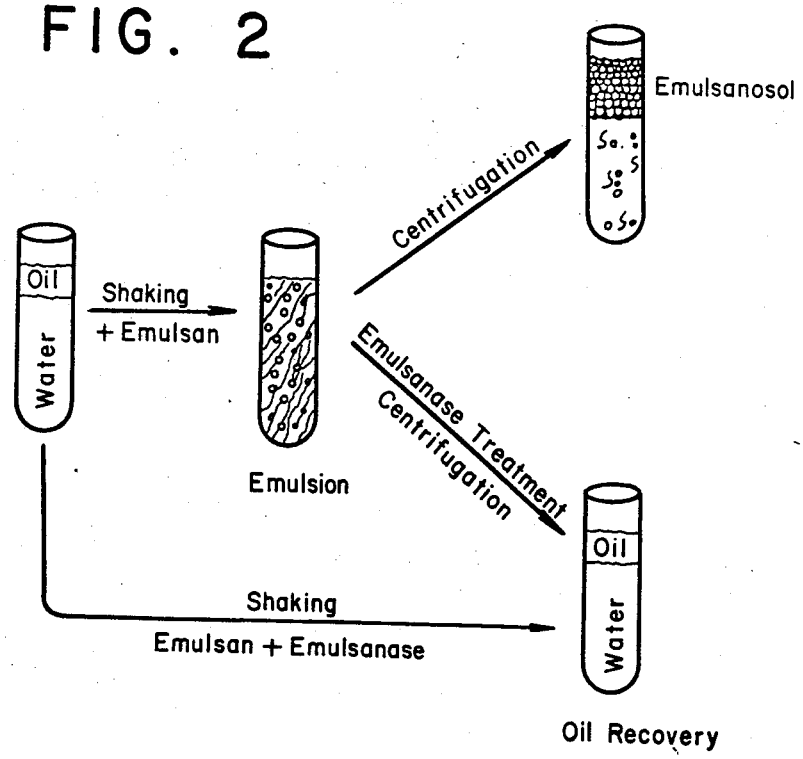
FIG. 2 is a schematic representation of the action of emulsanase on the formation and breakage of bioemulsifier-stabilized emulsions and of the formation of an emulsanosol by centrifugation.

The operation of emulsan and the application of this embodiment of the invention thereto may be readily understood by reference to the schematic representation of FIG. 2, wherein the application of agitation to an emulsan-containing oil and water mixture produces a stable oil-in-water emulsion. Centrifugation or prolonged standing may convert the emulsion to a creamy emulsanosol, which with the minor application of energy can be reconverted to a fully dispersed emulsion. Treatment of this emulsion with emulsanase will promote prompt emulsion collapse, with phase separation and the ready recovery of the oil component. Treatment of the initial oil-water-emulsan mixture with emulsanase would preclude any emulsion formation.

Figure 3:
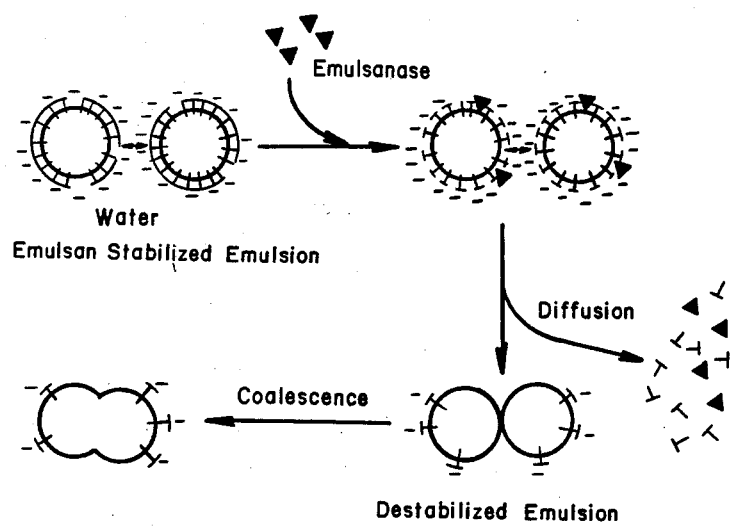
FIG. 3 is a schematic representation of the demulsification of emulsan-stabilized emulsions by emulsanase.

The action of this embodiment of the invention on preformed oil-in-water emulsions is illustrated further in the schematic drawing of FIG. 3. In FIG. 3 emulsanase, as indicated by closed triangles, attacks the emulsan shown as T's at the oil/water interface. By splitting relatively few bonds, emulsanase strips the emulsan molecules from the droplet surface, with subsequent oil coalescence.

This emulsan degrading process is applicable to emulsan in aqueous solution or to emulsan adherent to the hydrocarbon droplets in light hydrocarbon-in-water emulsions, and may be utilized with emulsan-stabilized emulsions of viscous hydrocarbons having hydrocarbon/water ratios of 90/10 or less wherein the viscous hydrocarbon is characterized by a viscosity of about $10^2$–$10^6$ centipoise or greater and otherwise generally, but not necessarily, characterized by API gravity of about 20° API or less, high metal content, high sulfur content, high asphaltene content and/or high pour point.

Broad limits of operational conditions may be employed for emulsanase, with temperatures ranging from about 5° C. to about 60° C., preferably in the range of about 30° C. to about 50° C. and more preferably around 40° C. The pH chosen may also vary widely, since although the pH optimum ranges from 7.0 to 8.0, activity was reduced by only 30% at pH 6.0 and 9.1. A useable pH range might thus be pH 5.5 to 9.5.

6.3. PREPARATION AND USE OF EMULSAN ENZYMATIC DEGRADATION PRODUCTS

The oligosaccharidic degradation products from the exhaustive treatment of emulsan with emulsanase may be used as the complete digestion mixture. Alternatively, they may be utilized as a subfraction thereof, such subfraction being obtained by standard biochemical fractionation techniques. This embodiment of the invention, as exemplified by the products of the action of YUV-1 emulsanase on emulsan, lies in the mixture of fragments obtained and not in particular molecular species. It may be that fragments with particular charge, size or other characteristics might prove especially useful in a given application, but such minor variations would be understood to fall within the scope of the invention.

Both the prevention of bacterial adhesion and its elimination where already present are an aspect of this embodiment of the invention. Although specific reference is made, by way of illustration, to the interference of adherence of A. calcoaceticus RAG-1 (ATCC 31012) cells, any microbial strain in which hydrophobic forces are important for adherence is intended. Such microorganisms include but are by no means limited to Escherichia coli, Salmonella typhimurium, Streptococcus pyogenes, Staphylococcus aureus, Serratia marcescens, Acinetobacter BD4, and numerous oral bacterial strains. Furthermore, the surfaces to which microbial adherence is to be prevented or eliminated include, but are not limited to, epithelial cells, hydrocarbon surfaces, dental enamel, polystyrene or any other hydrophobic surface.

It is also intended that these oligosaccharidic fragments may be used in solution. Alternatively, they may be incorporated into any neutral carrier medium, regardless of its composition or other properties.

7. EXAMPLES

7.1. ISOLATION AND GROWTH OF AN EMULSANASE-PRODUCING BACTERIUM

7.1.1. GROWTH OF A MIXED CULTURE FROM SOIL

A soil sample was suspended in a pH 7.2 minimal salt solution (MS medium) containing 22.2 g of dibasic potassium phosphate [$K_2HPO_4 \cdot 3H_2O$], 7.26 g of monobasic potassium phosphate, 8 g of ammonium sulfate, and 0.2 g of magnesium sulfate [$MgSO_4 \cdot 7H_2O$] per liter, and then inoculated into the same medium with 1.0% (w/v) yeast extract.

After incubation in Erlenmeyer flasks filled to 10–20% of capacity with shaking in a New Brunswick G-53 Gyrotory shaker at 150 rpm and at 30° C. for 12 hours, three successive transfers of incubation samples were made into MS medium with 0.1% (w/v) N-acetylgalactosamine, with each transfer incubated with shaking for 24 hours at 30° C. before the next was made. Further transfers were then made into MS medium with 0.1% (w/v) emulsan as the sole carbon and energy source, and the mixed culture was maintained either by transferring into emulsan medium at 3-day intervals or by centrifuging the mixed culture and then freezing the bacterial pellet at −21° C. This and subsequent experiments were performed with substantially deproteinized α-emulsan (residual protein content of about 1.0%), i.e., apo-α-emulsan. The choice of emulsan, however, was not critical since all the emulsans derived from A. calcoaceticus RAG-1 (ATCC 31012) have the same heteropolysaccharide structual backbone.

7.1.2. DEGRADATION OF EMULSAN BY THE MIXED CULTURES

Preliminary studies had suggested that the mixed bacterial culture could degrade emulsan, since the viscosity of emulsan medium decreased markedly with continued incubation. To demonstrate this ability more precisely, changes in the emulsifying activity and the viscosity of emulsan medium during incubation with the mixed culture were examined.

Figure 4:
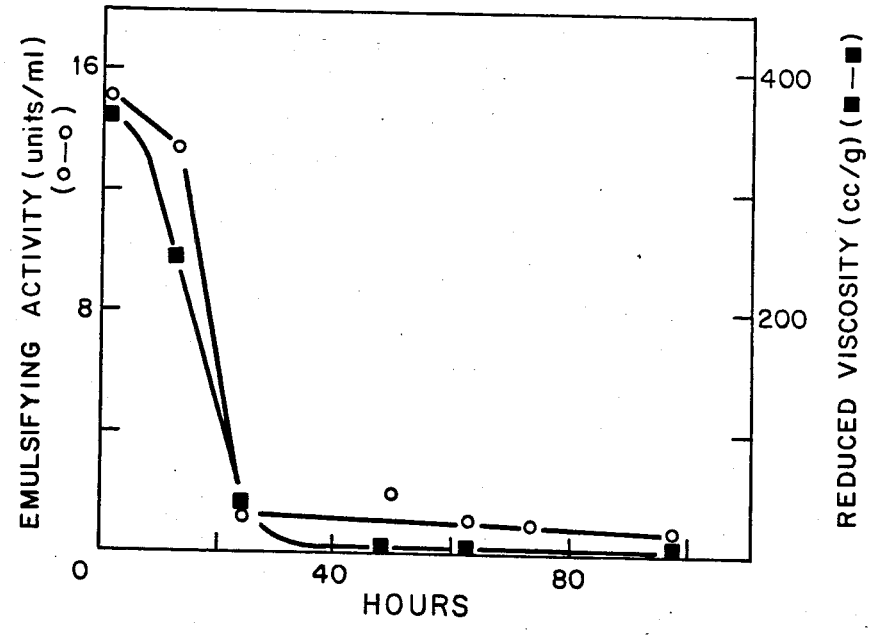
FIG. 4 is a graphical representation of the degradation of emulsan, showing decreases in emulsifying activity and viscosity in an emulsan medium as a function of time, during the growth of a mixed microbial culture isolated from soil.

The results of this work are shown in FIG. 4, where the data were based upon the incubation of an inoculate of the mixed bacterial culture in MS medium containing 0.73 mg/ml emulsan with gyrotory shaking at 30° C. At the indicated time intervals, aliquots were withdrawn for the analysis of viscosity and emulsifying activity.

Viscosity of samples was measured in standard Tris-magnesium buffer [20 mM Tris-hydrochloride with 10 mM $MgSO_4$ (pH 7.0)] in a PSL calibrated Cannon-Ubbelohde Semi-Micro Viscometer.

Emulsifying activity was measured in 100 ml flasks by combining 7.4 ml final volumes of emulsan solutions in standard Tris-magnesium buffer with 0.1 ml of a standard hydrocarbon mixture. This mixture contained equi-volume quantities of hexadecane and 2-methylnaphthalene. The assay mixture was then incubated at 30° C. with 160 strokes per minute reciprocal shaking for 60 min., when the mixture was transferred to a test tube for turbidity measurement in a Klett Summerson colorimeter fitted with a green filter. One unit per ml of emulsifying activity is defined as an amount of emulsifier that yields 100 Klett units in the assay.

7.1.3. DEGRADATION OF EMULSAN BY A MIXED CULTURE CELL-FREE SUPERNATANT FLUID

Figure 5:
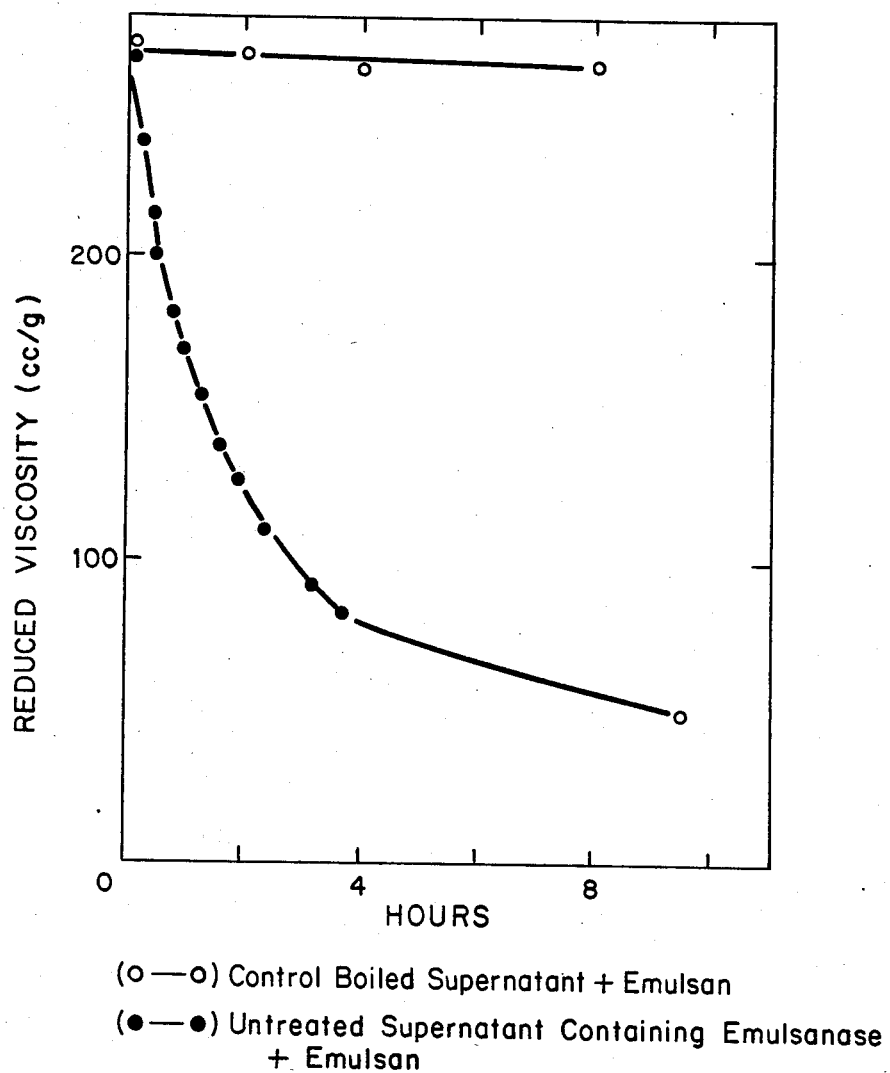
FIG. 5 is a graphical representation of emulsan degradation by a cell-free supernatant sample from the mixed microbial culture of FIG. 4 (upper curve), showing a reduction of viscosity as a function of time as compared to the control (lower curve)

Since a major objective of this work was to isolate an emulsan-degrading enzyme, it was important to determine whether the activity observed in the mixed culture was extracellular. The fact that the activity was at least partly extracellular is shown in FIG. 5. The data shown in FIG. 5 were obtained by growing the mixed culture on emulsan medium for 40 hours, centrifuging to pellet the cells, filtering the supernatant fluid through a 0.45 μm filter, and adding the fluid to an equal volume of a solution containing 1.46 mg/ml emulsan. The viscosity of the mixture was then determined after the indicated periods of incubation at 30° C. by the method described in 7.1.2. The emulsan-degrading activities of both untreated [closed circles] and control boiled [open circles] supernatant fluids were determined.

7.1.4. ISOLATION OF A PURE CULTURE OF AN EMULSAN-DEGRADING BACTERIUM FROM THE MIXED BACTERIAL CULTURE

The above studies showed that the mixed culture contained at least one bacterial species capable of degrading emulsan. Thus dilution of the mixed culture and growth of isolates would be expected to yield a pure emulsan-degrading bacterial strain.

To determine approximately how many colonies would have to be screened to isolate the desired bacterium, serial dilutions were made of a mixed culture grown for 3 days on emulsan medium. The initial cell concentration was determined by plating on nutrient agar (containing 2% Bacto agar, 1% Bacto-tryptone and 0.5% yeast extract), incubating for 2 days at 32° C., and counting the colonies. Aliquots of this mixed culture were then serially diluted into 1 ml of fresh emulsan medium, and the samples were incubated in test tubes with shaking at 30° C. Periodically, emulsan-degrading activity was estimated by a semi-quantitative micro assay method. In this assay, 50 μl ( aliquots of the incubated samples were added to 8 mm test tubes containing 0.5 ml of Tris-magnesium buffer [20 mM Tris-hydrochloride with 10 mM $MgSO_4$ (pH 7.0)] and 20 μl of equi-volume hexadecane and 2-methylnaphthalene. The tubes were then vortexed for 3 minutes, allowed to stand for 1 minute and examined visually for turbid, stable emulsions. Samples in which the emulsan had been degraded separated into hydrocarbon and water phases.

Table II summarizes these results, with +indicating emulsan degradation, and —indicating none.

TABLE II

EMULSAN DEGRADATION BY MIXED CULTURE SERIAL DILUTIONS

| Inoculum (bacteria/ml) | Emulsan Degradation | | | |
|---|---|---|---|---|
| | 15 hr. | 48 hr. | 96 hr. | 2 weeks |
| $8 \times 10^7$ | + | + | + | + |
| $8 \times 10^6$ | + | + | + | + |
| $8 \times 10^5$ | − | + | + | + |
| $8 \times 10^4$ | − | + | + | + |
| $8 \times 10^3$ | − | − | + | + |
| $8 \times 10^2$ | − | − | + | + |
| $8 \times 10^1$ | − | − | − | − |
| $8 \times 10^0$ | − | − | − | − |

The results shown in Table II suggested that the frequency of emulsion-degrading bacterium in the mixed culture was likely to be between 0.01 and 0.001. Since plating experiments showed that many colonies appeared similar, however, it seemed likely that a careful screening of 50 different isolates would yield the desired bacterium. Accordingly, 50 colonies were isolated by incubation on nutrient agar as described above.

One of these isolates, designated YUV-1, was able to degrade emulsan, as shown both by a loss in emulsifying activity and by a decrease in the viscosity of emulsan medium.

7.1.5. PROPERTIES OF THE YUV-1 BACTERIUM

Before classification, YUV-1 had been tentatively identified by Shoham et al. [Appl. Environ. Microbiol. 46: 573–579 (1983)] as a Zoogloea species. However, more complete classification indicates that YUV-1 is a Bacillus species. Although YUV-1 has a strong morphological resemblance to *Bacillus circulans*, it is not able to hydrolyze starch or to produce acid from carbohydrate. It is clear that it is an aerobic, gram-variable, sporulating, non-photosynthetic, rod-shaped bacterium about 4 μm in length and 1 μm in diameter, with rounded to pointed ends. YUV-1 bacteria usually appear alone, although some form short chains up to three organisms in length. When strain YUV-1 is grown on nutrient medium containing yeast extract, spores are not formed. When YUV-1 is grown on medium known to induce spore formation, a single, oval, subterminal, central endospore is formed per cell. When grown on nutrient agar (2% Bacto agar, 1% Bacto-tryptone and 0.5% yeast extract) for 2 days at 32° C., the strain produces raised, circular and colorless colonies of 1 to 2 mm diameter, with smooth edges.

Figure 6:
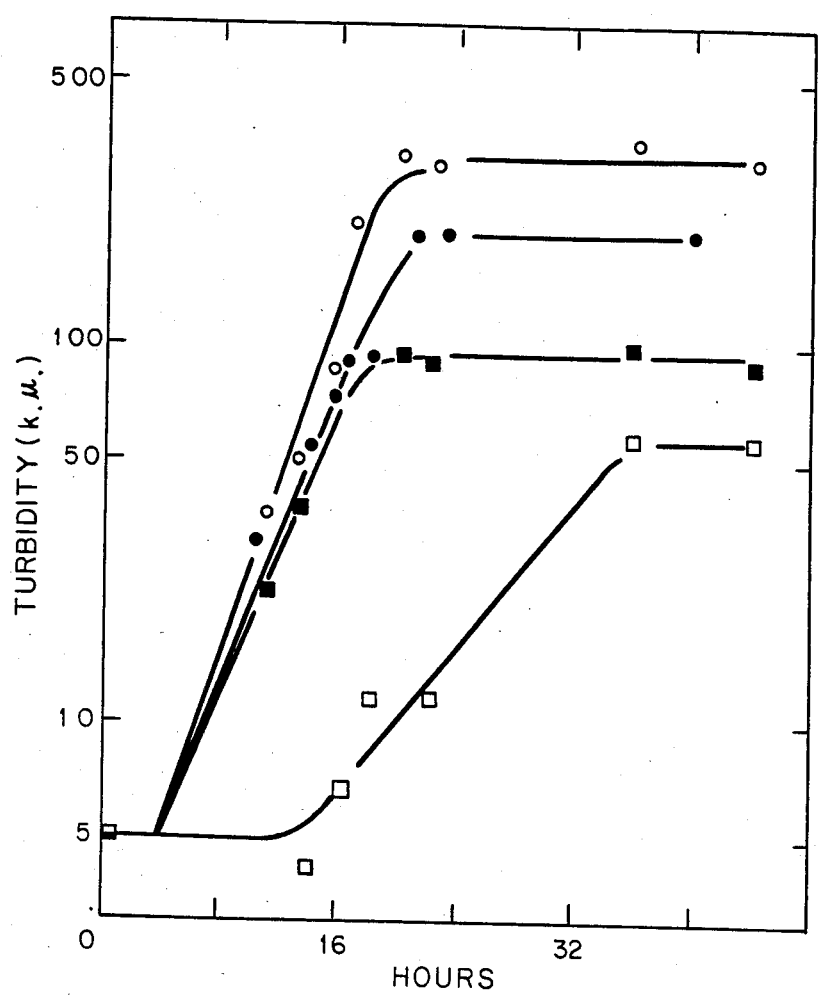
FIG. 6 is a graphical representation of the growth of YUV-1, an isolate from the mixed microbial culture, on medium supplemented with varying amounts (0-1.5%) of yeast extract, as a function of time.

YUV-1 can readily be grown in a liquid medium, as shown in FIG. 6. The data of FIG. 6 were obtained by incubating YUV-1 at 30° C. in Bacto-tryptone containing no supplement [open boxes], 0.5% yeast extract [closed boxes], 1.0% yeast extract [close circles], or 1.5% yeast extract [open circles]. At the indicated time intervals, growth was determined by measuring the turbidity of the cultures in a Klett Summerson photoelectric colorimeter (model 800-3) using a green filter. Dilutions were made as required to keep the readings within the linear range of the instrument.

Interestingly, although the mixed culture grew well on either emulsan medium or emulsan agar, the pure YUV-1 strain showed no significant growth in either. While the role of the yeast extract is not understood, it apparently supplies growth factors that replace those provided by other bacteria in the mixed culture. For convenience, YUV-1 was routinely maintained on nutrient agar (2.0% Bacto agar containing 1.0% Bacto-tryptone and 0.5% yeast extract).

7.2. PARTIAL PURFICATION AND CHARACTERIZATION OF EMULSANASE

7.2.1. ISOLATION OF EMULSANASE FROM A PURIFIED YUV-1 CULTURE

Although YUV-1 grows readily in complex media containing yeast extract (FIG. 6), the isolation of an enzyme from such complex media is more difficult than from minimal media. Furthermore, in the absence of emulsan YUV-1 produced no measurable emulsanase activity. Growth of the bacteria in emulsan-containing medium did lead to emulsanase production, but adequate quantities of pure emulsan for large scale emulsanase production in liquid culture were not available for this series of experiments.

To circumvent these problems YUV-1 was grown on lawns of *Acinetobacter calcoaceticus* RAG-1 on ethanol agar. Ethanol agar was prepared by adding 1.5 percent Nobel agar to the MS medium of 7.1.1, coating culture dishes with 30ml of the agar, and adding ethanol by placing 0.2 ml of the alcohol on a filter paper affixed to the culture dish cover. In use, the dishes were incubated inverted. Through this culturing arrangement, the *Acinetobacter calcoaceticus* RAG-1 grew and produced emulsan, which in turn stimulated emulsanase production by YUV-1.

Lawns of *A. calcoaceticus* RAG-1 were formed by streaking the cells on the above ethanol agar plates and then incubating at 32° C. for 12 hours. Then YUV-1 cells were added under sterile conditions, and the plates were further incubated for 3 days at 32° C. As the incubation progressed, growing translucent plaques appeared around the YUV-1 colonies, as secreted emulsanase degraded emulsan in the RAG-1 lawn, and after 3 days the plates were uniformly translucent.

To isolate the YUV-1 emulsanase, the agar was first cut into small pieces and then stirred with an equal volume of MS medium at 4° C. for 2 hours. The mixture was centrifuged for 30 minutes at 4,320×g, the clear supernatant fluid was reserved, and the pellet was extracted twice more in the same fashion. After pooling and further centrifugation of the supernatant fractions at 4,230×g for 30 minutes, the clarified extracts were concentrated and purified by one of three methods.

A fraction referred to as fraction A was obtained by adding 291 g of ammonium sulfate to 1 liter of the agar extract at 4° C. with stirring. After standing overnight at 4° C., the precipitate was recovered by centrifugation at 4,230×g for 30 minutes. The pellet, which was dissolved in 100 ml of MS medium, dialized extensively against cold MS medium, and stored at −40° C., contained 340 μg of protein per ml, as determined by the method of Lowry et al. [J. Biol. Chem 193, 265 (1951)] using bovine serum albumin as a standard.

Partially purified and concentrated fractions were also prepared by ultrafiltration. One fraction, called F-10, was obtained by filtering 360 ml of the agar extract through an Amicon XM-50 membrane in a stirred model 521 Amicon cell under 0.75 atmospheres of nitrogen at 4° C., until a final volume of 36 ml was obtained. The nonfilterable F-10 fraction contained 300 μg of protein per ml. Another fraction, designated F-2, was obtained in an identical manner except for the substitution of an Amicon PM-30 membrane and an overall reduction in volume of only 7-fold. This fraction contained 120 μg of protein per ml.

7.2.2 CHARACTERIZATION OF FRACTION F-10 EMULSANASE

Figure 7:
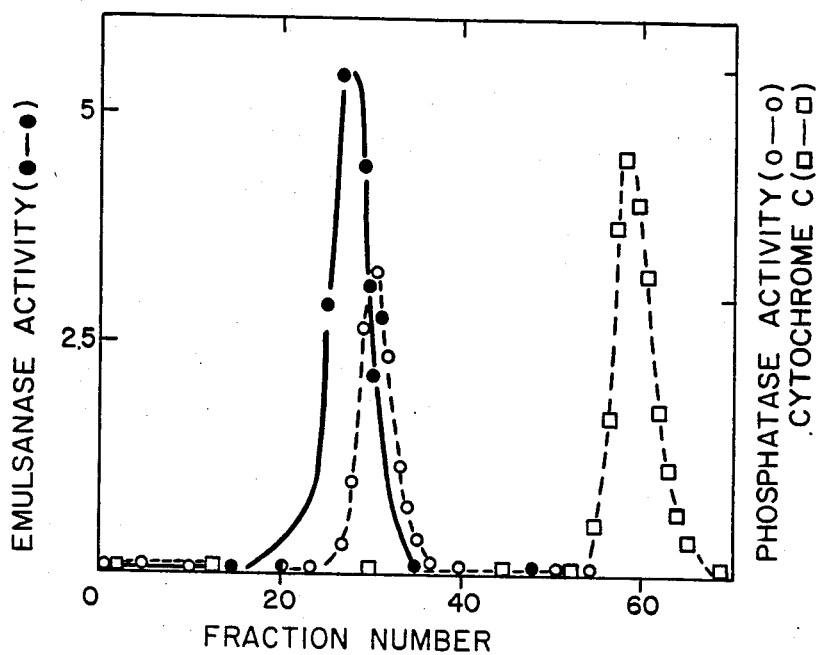
FIG. 7 is a graphical representation of the molecular size determination of emulsanase by gel filtration in Sephadex G-100, with cytochrome C and alkaline phosphatase as molecular weight standards.

The fact that YUV-1 emulsanase did not pass through an Amicon XM-50 filter suggested that its molecular weight was greater than 50,000 daltons. To more precisely establish the enzyme's size, the F-10 fraction was subjected to gel filtration chromatography as shown in FIG. 7. One ml of the F-10 enzyme preparation was first further purfied by gel filtration through a 1.5×50 cm Sephadex G-100 column in 50 mM phosphate buffer, pH 7.1. Fractions containing emulsanase activity, as shown by the ability of 10-μl samples to form plaques on a preformed lawn of RAG-1 cells incubated for 3 hours at 37° C., were pooled. Seven tenths of a ml of this pool, together with 200 μl of 5 mg/ml cytochrome C and 100 μl of 0.55 mg/ml alkaline phosphatase were then subjected to gel filtration as described above.

Cytochrome C [open boxes] was determined by measuring absorbance in a spectrophotometer at 409 nm. Phosphatase activity [open circles] was determined by release of p-nitrophenol from p-nitrophenyl phosphate, using the method described for alkaline phosphatase in the Worthington Enzyme Manual (1972). Emulsanase activity [closed circles] was determined by incubating 0.1 ml of each fraction with 1 mg of emulsan in 1 ml, with one unit defined as the amount of enzyme that can produce 1 μmole of reducing sugar per hour. By using the known molecular weights of cytochrome C (12,400 daltons) and alkaline phosphatase (86,000 daltons), the molecular weight of emulsanase was determined to be 89,000 daltons.

Partially purified F-10 YUV-1 emulsanase was also examined to determine its enzymatic properties. No proteinase activity was seen during incubation with casein as a substrate. Since emulsanase clearly degraded emulsan, however, the character of bond breakage was of interest. As noted in Section 6.2.1 above, the major components of emulsan are D-galactosamine and an unidentified amino uronic acid, with fatty acids and acetate bound to the polysaccharide backbone through O-ester and N-acyl linkages. Thus esterase, de-N-acetylase or glycosidase activity might cause emulsan degradation.

The results of functional group analysis for these possible activities are summarized in Table III. One ml of 1.0 mg/ml emulsan was incubated with 0.1 ml of F-10 emulsanase for 20 hours at 32° C., and aliquots were taken for enzymatic activity analysis. Esterase activity was determined by measuring O-esters by the method of Stern et al. [J. Clin. Pathol. 6, 158 (1953)], using acetohydroxymate as a standard. De-N-acetylase activity was determined by measuring free amino groups, using a modification of the trinitrobenzene sulfonate (TNBS) method of Habeef [Anal. Biochem. 14, 328 (1966)], with 0.2% TNBS and without sodium dodecyl sulfate. Glycosidase activity was determined by measuring reducing groups, by the ferricyanide method of Park et al. [J. Biol. Chem. 181:149–151 (1949)], with D-galactosamine as the standard.

TABLE III
ENZYMATIC ACTIVITIES OF FRACTION F-10 ON EMULSAN

| Enzymatic activity | Functional group test | Quantity (μmoles/mg) t=0 hrs | Quantity (μmoles/mg) t=20 hrs | Functional group released (μmoles/mg) |
|---|---|---|---|---|
| Esterase | O-ester | 0.59 | 0.615 | −0.025 |
| De-N—acetylase | Free amino groups | 0.09 | 0.08 | 0.01 |
| Glycosidase | Reducing groups | 0.04 | 0.40 | 0.36 |

The data in Table III show that the only measurable activity of emulsanase was glycosidase activity. Since there are about 4.5 μmoles of glycosidic linkages per mg of emulsan, approximately 8% of these bonds were broken. On average, the oligomers produced should thus contain about 12 residues.

The degradation of emulsan by YUV-1 emulsanase could proceed by either of two probable mechanisms—by hydrolysis to produce saturated oligosaccharides, or by elimination to yield oligosaccharides that are terminated at their non-reducing ends by $\alpha$, $\beta$-unsaturated uronic acids. An example of the latter mechanism is the enzymatic depolymerization of the "Vi" antigen, a 1,4-polymer of 2-deoxy-2-acetylamino-D-galacturonic acid, which McNicol and Baker [Biochemistry 9, 1017 (1970)] have shown results in the formation of the corresponding $\Delta^{4,5}$ unsaturated uronic acid. Spectrophotometric data support an elimination mechanism, since absorbance of the reaction mixture increases at 233 nm in parallel with the increase in reducing groups, as degradation proceeds. Absorbance at that wavelength would be expected to increase with the formation of double bonds. Furthermore, the digestion fragments reacted with thiobarbituric acid reagent as described by Albersheim et al. [Arch. Biochem. Biophys. 90, 46 (1960)], to produce products with absorption maxima at 440 and 550 nm. Such behavior is characteristic of $\alpha$, $\beta$-unsaturated uronides according to McNicol et al. [Biochemistry 9, 1017 (1970)].

The activity of YUV-1 emulsanase is not influenced by the addition of 1 mM calcium chloride or 10 mM EDTA. Thus divalent cations are not essential.

7.3 CORRELATION OF THE VISCOSITY, EMULSIFYING ACTIVITY AND MOLECULAR SIZE OF EMULSAN DURING ITS ENZYMATIC DEGRADATION

Figure 8:
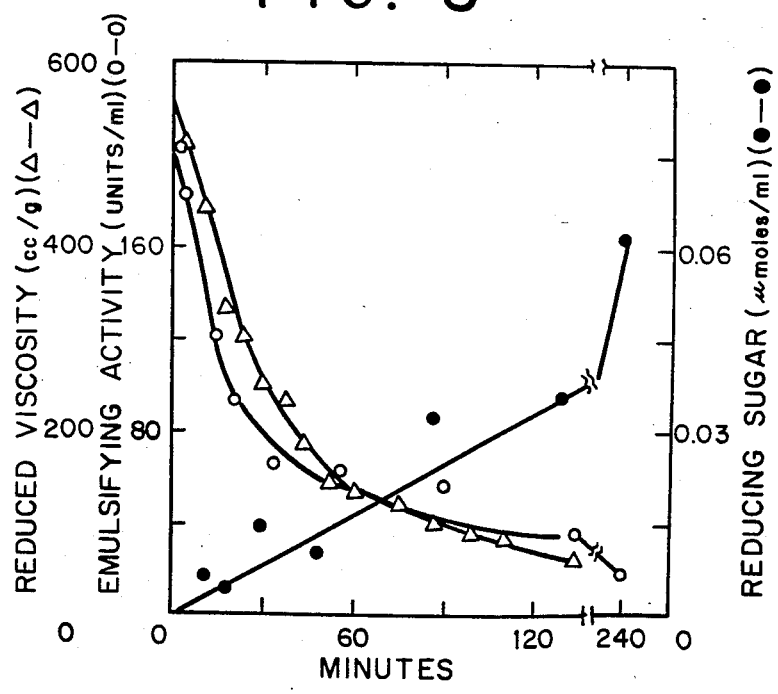
FIG. 8 is a graphical representation of the effects of emulsanase on emulsan, showing the concomitant formation of reducing groups and decreases in emulsifying activity and viscosity, all as a function of time.

The action of YUV-1 emulsanase on emulsan is characterized by a very rapid loss in visosity and emulsifying activity, and a concomitant increase in reducing sugars in the medium, as shown in FIG. 8. The data were obtained by incubating 0.5 mg per ml of emulsan with 17 μg per ml of fraction A emulsanase, at 30° C. and in 12 ml of Tris-magnesium buffer [20 mM Tris-hydrochloride with 10 mM MgSO4 (pH 7.0)]. At the indicated times, 1 ml samples were taken for the determination of emulsifying activity [open circles], viscosity [open triangles] and reducing sugars [closed circles], using the methods described above.

These same data are presented in Table IV, where molecular weight estimations are based on end group analysis. In these estimations, it has been assumed that there is no branching in the emulsan polymer and that the reducing power of the oligosaccharides produced is the same as that of the galactosamine standard.

TABLE IV
CORRELATIONS IN VISCOSITY, EMULSIFYING ACTIVITY AND REDUCING POWER

| Time (min) | Viscosity (% of initial) | Emulsifying activity (% of initial) | Reducing sugar (μm moles/mg emulsan) | Molecular weight (daltons) |
|---|---|---|---|---|
| 0 | 100 | 100 | 0 | $1 \times 10^6$ |
| 10 | 80 | 71 | 0.003 | 333,000 |
| 20 | 64 | 48 | 0.005 | 200,000 |
| 30 | 44 | 38 | 0.008 | 125,000 |
| 60 | 26 | 26 | 0.016 | 62,000 |
| 90 | 18 | 20 | 0.025 | 40,000 |
| 120 | 13 | 17 | 0.029 | 35,000 |
| 180 | 8.8 | — | 0.037 | 27,000 |
| 240 | — | 8.5 | 0.066 | 15,000 |

The data of Table IV show that a relatively minor degree of glycosidic bond breakage produces major changes in emulsion viscosity and emulsifying activity. Thus after 30 minutes of incubation, when only approximately 8 bonds per molecule had on average been broken, the viscosity and emulsifying activity of emulsan were only 44 and 38 percent of their initial values, respectively. These data clearly suggest that YUV-1 emulsanase is an endoglycosidase, and that the intact high molecular weight structure of emulsion is essential to its bioemulsifying activity.

7.4. BREAKAGE OF PREFORMED EMULSIONS BY EMULSANASE

Figure 9:
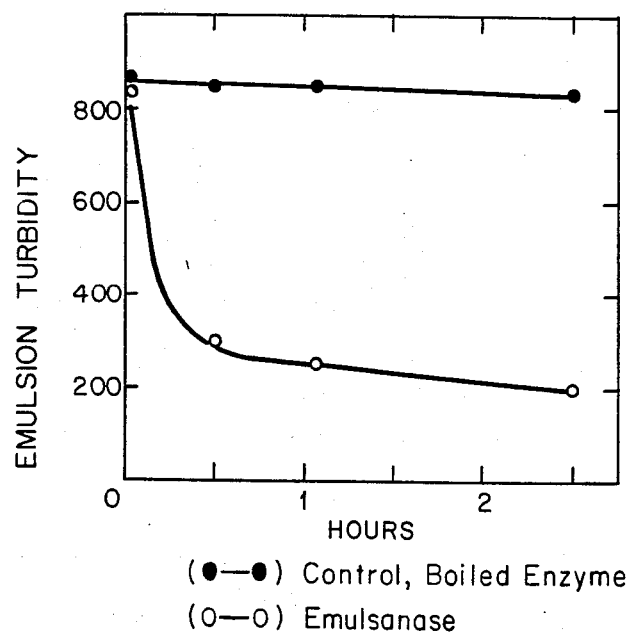
FIG. 9 is a graphical representation of the breakage of an emulsan-stablized emulsion by emulsanase (lower curve), showing the reduction in emulsion turbidity as a function of time as compared to a control (upper curve)

As shown above, YUV-1 emulsanase readily degrades emulsan that is free in solution. To determine whether the enzyme could also attack emulsan bound to the hydrocarbon/water interface in preformed emulsions, an experiment was performed, the results of which are illustrated in FIG. 9. Hydrocarbon-in-water emulsions were prepared by shaking mixtures containing 800 μg of emulsan and 0.5 ml of equi-volume hexadecane and 2-methylnaphthalene, all in 9.3 ml of Tris-magnesium buffer [20 mM Tris-hydrochloride with 10 mM MgSO4 (pH 7.0)], in 100 ml Erlenmeyer flasks at 30° C. for 15 minutes. Nine and a half ml aliquots were then combined in Klett tubes with 17 μg of fraction A emulsanase per ml [open circles], or with an equal amount of boiled enzyme as a control [closed circles], and the samples were incubated without shaking at 30° C. At the indicated times, samples were mixed gently by hand, allowed to stand for 30 seconds, and turbidity was determined as described above.

Emulsion breakage was rapid, reaching 70 percent after only 60 minutes. Even after 24 hours, a small amount of turbidity remained, but this was probably due not to emulsan stabilization, but to the presence of other proteins in the mixture. There was no change in turbidity in the boiled-enzyme control.

The ready breakage of emulsan-stabilized emulsions by YUV-1 emulsanase suggested that a high degree of hydrocarbon recovery should be possible. To investigate this possibility, an experiment that is summarized in FIG. 10 was performed. The data of FIG. 10 were obtained by preparing hydrocarbon-in-water emulsions containing 9 ml of Tris-magnesium buffer, pH 7.0, 0.8 ml of equi-volume hexadecane and 2-methylnaphthalene, and 0.75 ml of 1 mg per ml emulsan, incubated as described for FIG. 9. The emulsions were then transferred to Klett tubes and incubated with varying concentrations of fraction A emulsanase at 30° C. After 45 minutes, the samples were centrifuged for 6 minutes at 1,500 rpm, and the volumes of the clear hydrocarbon [open circles] and creamy emulsanosol [closed circles] phases were measured.

With 17 μg per ml emulsanase, hydrocarbon recovery exceeded 90%, and the hydrocarbon was clear and refractory to dispersal in water upon shaking, as it had originally been before emulsan treatment.

7.5 CHARACTERIZATION OF THE PRODUCTS OF THE EXHAUSTIVE ENZYMATIC DEGRADATION OF EMULSAN

When emulsan is incubated with sufficient YUV-1 emulsanase for an adequate period of time, a degree of degradation is achieved that cannot be increased either by incubation for a longer time or by the addition of fresh emulsanase. To characterize these limit-digest products, an exhaustively digested emulsan sample was fractionated by gel filtration chromatography as shown in FIG. 11. The data shown in FIG. 11 were based on the fractionation of part of 80 mg of emulsan that had been incubated with 1 mg of fraction A emulsanase for 5 days in 20 ml of 5 mM Tris buffer, pH 7.5, at 37° C. in a sealed tube. Following the incubation, 2 ml of the mixture were subjected to chromatography in a 1.1×150 cm Bio-Gel P-6 column in 5 mM Tris buffer at a flow rate of 20 ml per hour. Two-milliliter fractions were collected, and aliquots were analyzed for absorbance at 233 nm and for reducing sugars, as described above.

Fractions from the gel chromatography shown in FIG. 11 were then pooled as shown and subjected to further analysis. Reducing sugars and ester groups were determined as described above, and molecular weight ranges of the pooled fractions were estimated by elution positions. These molecular weight estimates may be inaccurate, since appropriate uronic acid oligosaccharide markers of known molecular weight were not available. The results of these analyses are summarized in Table V.

TABLE V
ANAYLSIS OF CHROMATOGRAPHED EMULSANASE LIMIT-DIGEST PRODUCTS

| Fraction (from FIG. 11) | Absorbance at 233 nm (total units) | Reducing Sugars (μmoles) | Ester Groups (μmoles) | Estimated Molecular Weight |
|---|---|---|---|---|
| A (24-29) | 3.72 | 0.75 | 1.06 | 4,500-6,000 |
| B (30-33) | 4.33 | 0.94 | 1.84 | 3,700-4,300 |
| C (34-37) | 2.68 | 0.58 | 0.96 | 3,000-3,600 |
| D (42-44) | 1.14 | 0.25 | 0.47 | 2,000-2,400 |

7.6 INHIBITION OF BACTERIAL ADHERENCE BY THE ENZYMATIC DEGRADATION PRODUCTS OF EMULSAN

As described in Section 2.3 above, intact emulsan can prevent the adherence of bacteria to hydrophobic surfaces, including the surfaces of hydrocarbons and epithelial cells. Furthermore, emulsan can desorb bacteria that are already adhering to such surfaces. It was thus of importance to determine whether the products of the exhaustive enzymatic degradation of emulsan retained these properties. To investigate this possibility, methods were used for cell preparation and assay that have been described in detail by Rosenberg et al. [Infect. Immun. 33, 29 (1981)].

7.6.1. INTERFERENCE WITH ADHESION TO EPITHELIAL CELLS

*A. calcoaceticus* RAG-1 cells ($1.0 \times 10^9$ cells per ml) and human buccal epithelial cells ($1.1 \times 10^6$ cells per ml) were incubated together for 15 minutes at 37° C., with or without emulsan that had been exhaustively degraded by YUV-1 emulsanase. The degraded emulsan used was that illustrated in FIG. 11, either as the complete digest mixture (50 μg per ml final concentration) or as the fractionated Bio-Gel P-6 pool B (50 μg per ml). Following the incubation, the epithelial cells were filtered to remove unbound bacteria, and then stained and scored for bacterial binding under a bright-field microscope as described by Rosenberg et al. [Infect. Immun. 33, 29 (1981)]. With both emulsan digest samples, the binding of *A. calcoaceticus* RAG-1 was reduced by 70 to 80%, compared to the untreated controls. This same degree of diminished adherence was obtained when the bacterial cells were first permitted to bind to the epithelial cells, and the emulsan degradation products were then added.

7.6.2. INTERFERENCE WITH ADHESION TO HYDROCARBONS

As shown by Rosenberg et al., supra, the binding of bacteria to liquid hydrocarbons may readily be demonstrated by suspending the cells in aqueous medium, layering the hydrocarbon over the cell suspension, mixing the two phases carefully, and then spectrophotometrically measuring the turbidity in the aqueous phase after phase separation. Adherent cells rise with the hydrocarbon, forming a creamy upper layer. Thus substantial cell binding to the hydrocarbon phase will produce a corresponding decrease in aqueous phase turbidity.

Using this method, about $10^9$ *A. calcoaceticus* RAG-1 cells were suspended in 1.2 ml of buffer at 30° C., with or without either the exhaustively degraded α-emulsan mixture (50 μg per ml final concentration) or the Bio-Gel pool B fraction (50 μg per ml final concentration). The suspension was then overlaid with 0.1 ml of hexadecane and mixed under controlled conditions for 120 seconds. After allowing for phase separation, the aqueous phase was withdrawn and its absorbance at 400 nm was measured. In the controls, the degree of binding of the bacteria to the hexadecane was greater than 90%. With either of the emulsan digest samples, the degree of bacterial binding was only 10 to 20%. This was true whether or not the binding was established before or after the emulsan digest additions. It should be added that the emulsanase-digested products did not emulsify the hexadecane, which otherwise would have interfered with the assay for bacterial turbidity.

Many modifications and variations of this invention may be made without departing from its spirit and scope and will become apparent to those skilled in the art from the foregoing description. The specific embodiments described herein are offered by way of example only, and the invention is limited only by the terms of the appended claims.

7.7. DEPOSIT OF MICROORGANISM

The YUV-1 emulsanase-producing bacterial strain has been deposited with the Agricultural Research Culture Collection (NRRL), Peoria, Ill. and has been assigned the accession number NRRL B-15617. A culture of the deposited microorganism will be made available to the public upon the grant of a patent based upon the present application. The invention described and claimed herein is not to be limited in scope by the strain of microorganism deposited, since the deposited embodiment is intended as a single illustration of one aspect of the invention and any equivalent microorganisms which produce functionally equivalent enzymes are within the scope of the invention.

We claim:

1. A microbial enzyme which degrades bioemulsifiers, said bioemulsifiers being lipopolysaccharides which bind predominantly at hydrocarbon/water interfaces surrounding hydrocarbon droplets dispersed in hydrocarbon-in-water emulsions and effectively stabilize said emulsions by substantially preventing coalescence of individual hydrocarbon droplets, and which enzyme yields lipo-oligosaccharide end-products retaining essentially no bioemulsifier activity compared to the lipopolysaccharide bioemulsifier.

2. The microbial enzyme of claim 1 wherein the lipopolysaccharide bioemulsifier is a lipopoly-[D-galactosamine/aminouronic acid]-saccharide.

3. A microbial enzyme which degrades emulsan bioemulsifiers, said emulsan bioemulsifiers being lipoheteropolysaccharides which bind predominantly at hydrocarbon/water interfaces surrounding hydrocarbon droplets dispersed in hydrocarbon-in-water emulsions and effectively stabilize said emulsions by substantially preventing coalescence of individual hydrocarbon droplets, and which enzyme yields lipohetero-oligosaccharide end-products retaining essentially no bioemulsifier activity compared to the emulsan bioemulsifier.

4. The enzyme of claim 3 which acts as a glycosidase.

5. The enzyme of claim 4 which acts as an endoglycosidase.

6. The enzyme of claim 4 or 5 which acts as a hydrolase and yields saturated lipohetero-oligosaccharide end-products.

7. The enzyme of claim 4 or 5 which acts as an eliminase and yields lipohetero-oligosaccharide end-products, which end-products are terminated at their non-reducing ends by $\alpha, \beta$-unsaturated uronic acids.

8. The enzyme of claim 3 which degrades an emulsan selected from the group consisting of $\alpha$-emulsan, $\beta$-emulsan, $\Psi$-emulsan, apo-$\alpha$-emulsan, apo-$\beta$-emulsan, and apo-$\Psi$-emulsan.

9. A microbial enzyme capable of selectively recognizing a poly-(D-galactosamine/aminouronic acid)-saccharide backbone of an emulsan bioemulsifier and cleaving glycosidic bonds in the emulsan bioemulsifier at least one nonterminal position to yield lipohetero-oligosaccharide fragments having discrete molecular weight, generally ranging from about 1,000 to about 60,000 daltons, said enzyme having activity in a pH range from about pH 5.5 to about pH 9.5, and in a temperature range from about 5° C. to about 60° C., having a molecular weight of around 84,000 daltons as measured by gel filtration chromatography, and produced by Bacillus sp. strain YUV-1, NRRL B-15617.

10. The enzyme of claim 9 which acts by an endoglycosidic elimination mechanism as determined spectrophotometrically.

11. The enzyme of claim 9 having an optimal pH range from about pH 7.0 to about pH 8.0 and an optimal temperature range from about 30° C. to about 50° C.

12. The enzyme of claim 9 wherein the emulsan bioemulsifier cleaved by said enzyme is selected from the group consisting of $\alpha$-emulsan, $\beta$-emulsan, $\Psi$-emulsan, apo-$\alpha$-emulsan, apo-$\beta$-emulsan and apo-$\Psi$-emulsan.

13. A substantially pure culture of bacterial Bacillus sp. strain YUV-1, NRRL B-15617.

14. A process for producing an emulsan-degrading enzyme which comprises: (A) inoculating an aqueous fermentation medium consisting essentially of sources of carbon, nitrogen, mineral salts, vitamins and an effective amount of an emulsan for enzyme induction with a culture of bacterial strain YUV-1, NRRL B-15617; (B) aerobically growing the microorganism in such fermentation medium for a period of time sufficient to produce emulsan-degrading enzymes; and (C) isolating the emulsan-degrading enzyme from said medium.

15. The process of claim 14 wherein the sources of carbon, nitrogen, mineral salts and vitamins are provided by yeast extract.

16. The process of claim 15 wherein the yeast extract is added to the fermentation medium at a concentration of about 5 grams per liter to about 20 grams per liter.

17. The process of claim 15 wherein an additional source of carbon is supplied by glucose used at a concentration from about 5 grams per liter to about 10 grams per liter.

18. The process of claim 14 wherein the amount of emulsan used for enzyme induction is about one gram per liter.

19. The process of claim 14 wherein the emulsan-degrading enzyme is isolated from the medium by separating out the microbial cell mass by filtration, centrifugation or decantation and partially purifying the enzyme from the cell-free medium by ammonium sulfate precipitation or ultrafiltration.

20. A method for enzymatically degrading an emulsan which comprises contacting in a reaction vessel an amount of an emulsan with an amount of the emulsan-degrading enzyme of claim 3 or 9 at an emulsan:enzyme ratio of about 25:1 to about 80:1 by weight in an aqueous buffer with a pH from about pH 7.0 to about pH 8.0 at a temperature from about 30° C. to about 50° C. for a period of time sufficient to yield lipo-oligosaccharide end-products ranging in size from about 1,000 to about 60,000 daltons.

21. The method of claim 20 wherein the emulsan is selected from the group consisting of $\alpha$-emulsan, $\beta$-emulsan, $\Psi$-emulsan, apo-$\alpha$-emulsan, apo-$\beta$-emulsan and apo-$\Psi$-emulsan.

22. The method of claim 20 wherein the buffer is Tris-magnesium buffer.

23. The method of claim 20 wherein the emulsan and the emulsan-degrading enzyme are contacted for a period of time ranging from about one hour to about 5 days.

24. A method for enzymatically breaking a lipopolysaccharide bioemulsifier-stablilized hydrocarbon-in-water emulsion which comprises introducing into the aqueous phase of a lipopolysaccharide bioemulsifier-stabilized hydrocarbon-in-water emulsion an effective amount of the microbial enzyme of claim 1, said amount being sufficient to degrade the lipopolysaccharide bioemulsifier predominantly located at the hydrocarbon/water interface surrounding hydrocarbon droplets in the emulsion to effect hydrocarbon coalescence and phase separation.

25. The method of claim 24 wherein the hydrocarbon-in-water emulsion comprises a viscous hydrocarbon characterized by a viscosity of about $10^2$ to about $10^6$ centipoise or greater at a hydrocarbon/water ratio of about 90/10 or less.

26. A method for enzymatically breaking an emulsan-stabilized hydrocarbon-in-water emulsion which comprises introducing into the aqueous phase of an emulsan-stabilized hydrocarbon-in-water emulsion an effective amount of the microbial enzyme of claims 3 or 9, said amount being sufficient to degrade the emulsan predominantly located at the hydrocarbon/water interface surrounding hydrocarbon droplets in the emulsion to effect hydrocarbon coalescence and phase separation.

27. The method of claim 26 wherein the hydrocarbon-in-water emulsion comprises a viscous hydrocarbon characterized by a viscosity of about $10^2$ to about $10^6$ centipoise or greater at a hydrocarbon/water ratio of about 90/10 or less.

28. The method of claim 26 wherein the emulsan is selected from the group consisting of $\alpha$-emulsan, $\beta$-emulsan, $\Psi$-emulsan, apo-$\alpha$-emulsan, apo-$\beta$-emulsan and apo-$\Psi$-emulsan.

29. The method of claim 26 wherein the hydrocarbon of the emulsan-stabilized hydrocarbon-in-water is an equi-volume mixture of hexadecane and 2-methylnaphthalene.

* * * * *